(12) United States Patent
Morii et al.

(10) Patent No.: US 12,310,925 B2
(45) Date of Patent: May 27, 2025

(54) PHARMACEUTICAL MANAGEMENT SYSTEM

(71) Applicant: PHC Holdings Corporation, Tokyo (JP)

(72) Inventors: Hideyuki Morii, Ehime (JP); Yoshinori Hosoe, Ehime (JP); Yukitoshi Miyamoto, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 301 days.

(21) Appl. No.: 17/957,769

(22) Filed: Sep. 30, 2022

(65) Prior Publication Data

US 2023/0029147 A1 Jan. 26, 2023

Related U.S. Application Data

(63) Continuation of application No. PCT/JP2021/008257, filed on Mar. 3, 2021.

(30) Foreign Application Priority Data

Apr. 6, 2020 (JP) ................ 2020-068339

(51) Int. Cl.
*G16H 20/13* (2018.01)
*A61J 7/04* (2006.01)
(52) U.S. Cl.
CPC .......... *A61J 7/0472* (2013.01); *A61J 7/0436* (2015.05); *G16H 20/13* (2018.01); *A61J 2200/44* (2013.01); *A61J 2205/00* (2013.01)
(58) Field of Classification Search
CPC ............. B65G 1/137; A61J 3/00; A47B 81/00
See application file for complete search history.

(56) References Cited

U.S. PATENT DOCUMENTS

2009/0294467 A1* 12/2009 Yuyama ............ G07F 11/62
221/8
2011/0172815 A1* 7/2011 Kim ............ G07F 17/0092
361/679.01

(Continued)

FOREIGN PATENT DOCUMENTS

JP 2000-105149 A 4/2000
WO 2020/031499 A1 2/2020

OTHER PUBLICATIONS

International Search Report issued on May 25, 2021 in International Patent Application No. PCT/JP2021/008257, with English translation.

(Continued)

*Primary Examiner* — Gene O Crawford
*Assistant Examiner* — Ayodeji T Ojofeitimi
(74) *Attorney, Agent, or Firm* — Rimon P.C.

(57) ABSTRACT

A pharmaceutical management system includes: at least one pharmaceutical storage box to store at least one pharmaceutical having corresponding at least one IC tag attached thereto; a reading device to read information stored in the IC tag, the information representing the pharmaceutical; a controller to obtain the information of the IC tag from the reading device, to manage the pharmaceutical; and a pharmaceutical refrigerator to store the pharmaceutical storage box to refrigerate the pharmaceutical, the controller including a first and second entry/exit monitoring unit to monitor entry/exit of the pharmaceutical into/from the pharmaceutical storage box; and after monitoring by the first entry/exit monitoring unit, a state of entry of the pharmaceutical into the pharmaceutical storage box is determined based on a result of monitoring by the second entry/exit monitoring unit.

5 Claims, 7 Drawing Sheets

(56) References Cited

U.S. PATENT DOCUMENTS

| | | | |
|---|---|---|---|
| 2015/0127145 A1* | 5/2015 | Kim | G16H 40/67 700/235 |
| 2015/0203297 A1* | 7/2015 | Manning | B65G 1/133 700/218 |
| 2017/0083686 A1* | 3/2017 | Hawkins | G06Q 10/087 |
| 2021/0161766 A1 | 6/2021 | Okuda et al. | |

OTHER PUBLICATIONS

Extended European Search Report dated Jul. 5, 2023 issued in the corresponding European Patent Application No. 21783673.3.

\* cited by examiner

PHARMACEUTICAL MANAGEMENT SYSTEM

CROSS-REFERENCE TO RELATED APPLICATIONS

This is a continuation application of International Patent Application No. PCT/JP2021/008257 filed Mar. 3, 2021, which claims the benefit of priority to Japanese Patent Application No. 2020-068339 filed Apr. 6, 2020, the entire contents of each of which are incorporated herein by reference.

BACKGROUND

Technical Field

The present disclosure relates to pharmaceutical management systems.

Description of the Related Art

For example, pharmaceutical refrigerators are known for storing and managing pharmaceuticals in an environment with a predetermined refrigerating temperature (see, for example, Japanese Patent Application Publication No. 2000-105149).

Medical institutions put pharmaceutical manufacturers' pharmaceuticals delivered from pharmaceutical wholesalers into a pharmaceutical refrigerator and store/manage them under an environment at optimum refrigerating temperatures for the pharmaceuticals. Under the current circumstances, however, pharmaceutical manufacturers and wholesalers do not fully grasp information on the medical institution side, such as how the pharmaceuticals are temperature-controlled and when they are dispensed for prescriptions. Thus, pharmaceuticals may not be smoothly distributed among medical institutions, pharmaceutical wholesalers, and pharmaceutical manufacturers.

SUMMARY

A primary aspect of an embodiment of the present disclosure is a primary aspect of an embodiment of the present disclosure is a pharmaceutical management system comprising: at least one pharmaceutical storage box to store at least one pharmaceutical having corresponding at least one IC tag attached thereto; a reading device to read information stored in the IC tag, the information representing the pharmaceutical; a controller to obtain the information of the IC tag from the reading device, to manage the pharmaceutical; and a pharmaceutical refrigerator to store the pharmaceutical storage box to refrigerate the pharmaceutical, the controller comprising a first entry/exit monitoring unit to monitor entry/exit of the pharmaceutical into/from the pharmaceutical storage box by obtaining the information of the IC tag, during a first period, in response to open/close information indicating that a door of the pharmaceutical refrigerator has been closed from an open state; and a second entry/exit monitoring unit to monitor entry/exit of the pharmaceutical into/from the pharmaceutical storage box by obtaining the information of the IC tag, during a second period, after monitoring by the first entry/exit monitoring unit, and wherein a state of entry of the pharmaceutical into the pharmaceutical storage box is determined based on a result of monitoring by the second entry/exit monitoring unit.

Other features of the present disclosure will become apparent from the following description and the drawings.

DETAILED DESCRIPTION

At least the following matters will be apparent from illustration in the description and the attached drawings.

===Pharmaceutical Management Systems===

Medical institutions sometimes handle pharmaceuticals that are expensive and need strict distribution control (e.g., antineoplastic agents, therapeutic agents for hemophilia, plasma preparations, an albumin preparations, therapeutic agents for autoimmune, vaccines, therapeutic agents for rare diseases, and the like. Hereinafter, also referred to as "specialty pharmaceuticals" for convenience of explanation) as pharmaceutical manufacturers' pharmaceuticals delivered from pharmaceutical wholesalers. In such cases, the medical institutions need to strictly control the temperature of a pharmaceutical refrigerator such that the specialty pharmaceuticals stored therein are kept at their optimum temperatures. Under the current circumstances, however, pharmaceutical manufacturers and wholesalers do not sufficiently grasp information on the medical institution side, as to how specialty pharmaceuticals are temperature-controlled. Accordingly, the medical institutions are not allowed to return specialty pharmaceuticals to pharmaceutical manufacturers or wholesalers, which would possibly hinder the overall distribution of pharmaceuticals including specialty pharmaceuticals among medical institutions, pharmaceutical wholesalers, and pharmaceutical manufacturers. Thus, in order to achieve the smooth distribution of pharmaceuticals among medical institutions, pharmaceutical wholesalers, and pharmaceutical manufacturers, pharmaceutical management systems according to an embodiment of the present disclosure are provided.

Figure 1:
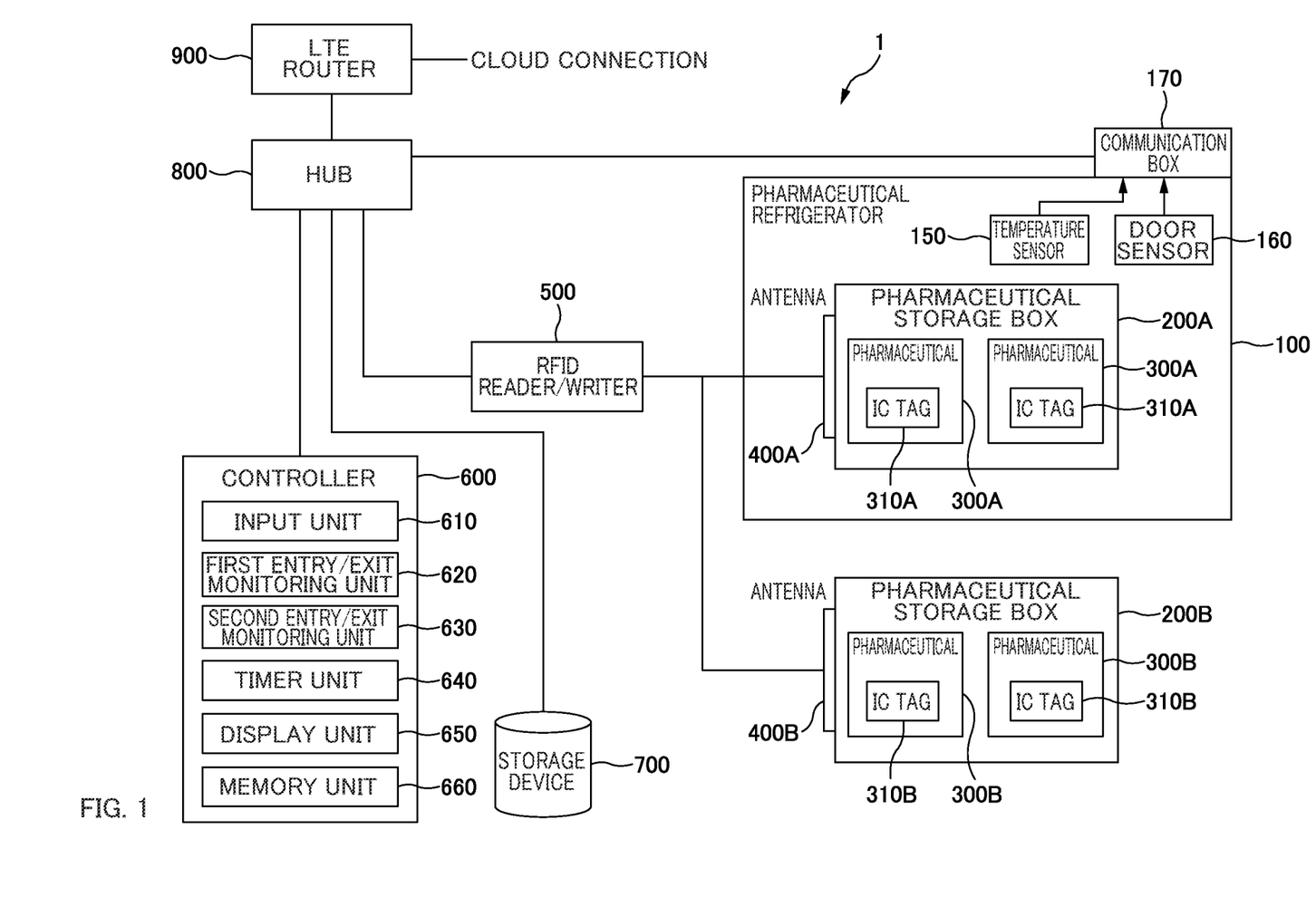
FIG. 1 is a block diagram illustrating an example of a pharmaceutical management system according to an embodiment of the present disclosure.

FIG. 1 is a block diagram illustrating an example of a pharmaceutical management system according to an embodiment of the present disclosure.

In FIG. 1, a pharmaceutical management system 1 includes a pharmaceutical refrigerator 100, pharmaceutical storage boxes 200 (200A, 200B), IC tags 310 (310A, 310B) attached to respective pharmaceuticals 300 (300A, 300B), antennas 400 (400A, 400B), an RFID reader/writer 500, a controller 600, and a storage device 700. Details of these components will be described later.

<<Pharmaceutical Refrigerator>>

Figure 2:
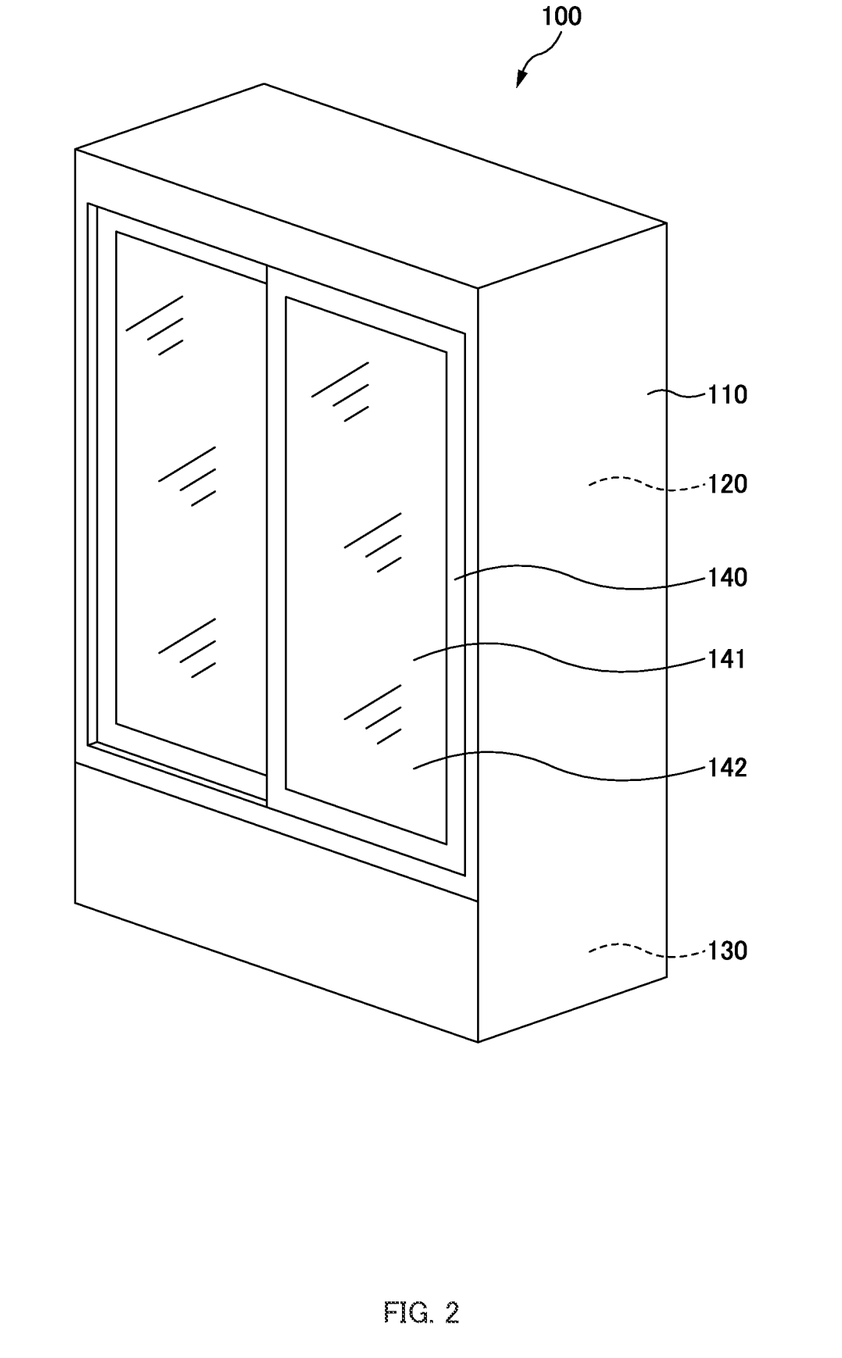
FIG. 2 is a perspective view illustrating an example of a pharmaceutical refrigerator to be used in a pharmaceutical management system according to an embodiment of the present disclosure.
Figure 3:
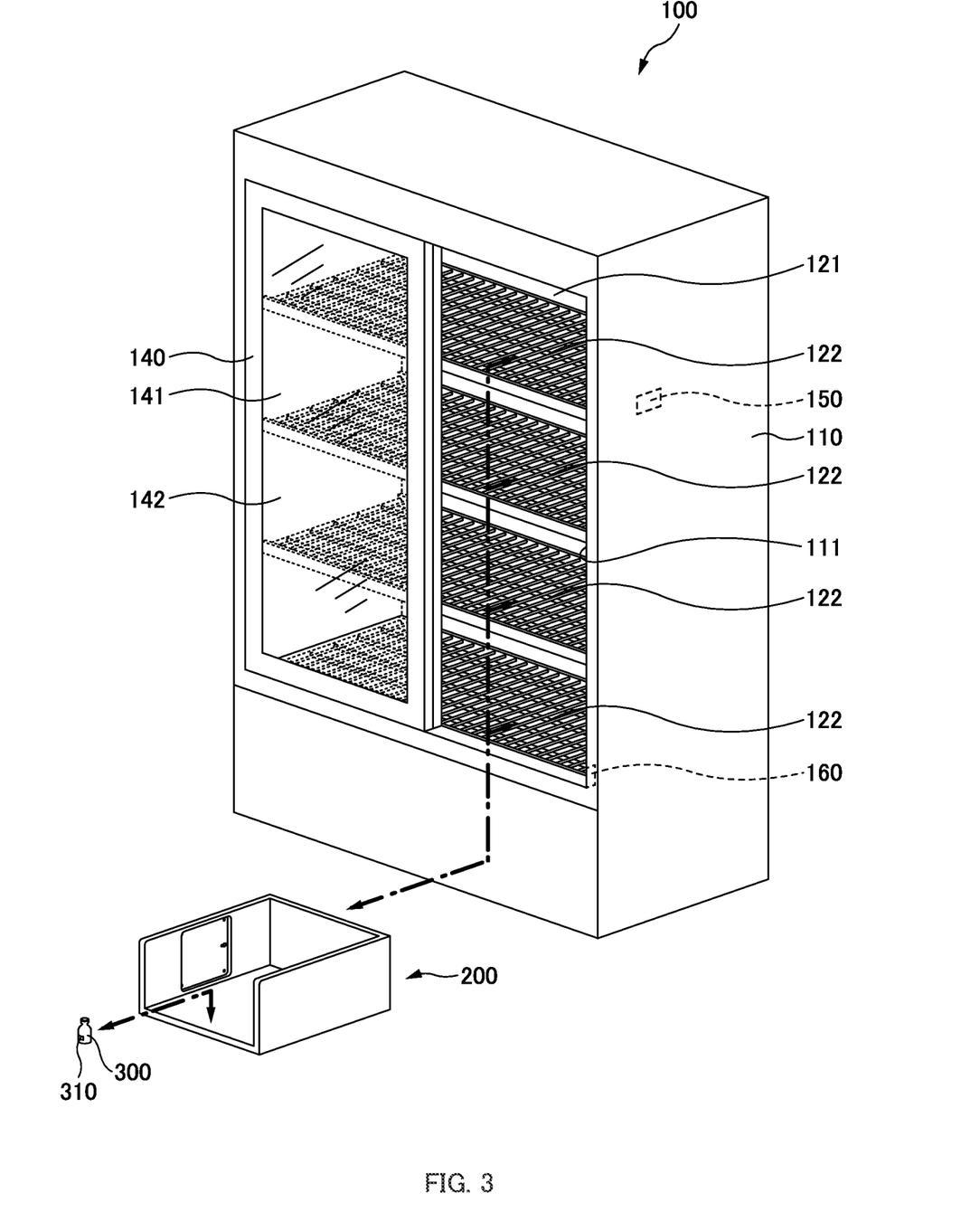
FIG. 3 is a perspective view illustrating how a pharmaceutical storage box is moved in and out of a pharmaceutical refrigerator illustrated in FIG. 2.

FIG. 2 is a perspective view illustrating an example of a pharmaceutical refrigerator to be used in the pharmaceutical management system according to an embodiment of the present disclosure. FIG. 3 is a perspective view illustrating how a pharmaceutical storage box is moved in and out of the pharmaceutical refrigerator illustrated in FIG. 2.

The pharmaceutical refrigerator 100 is a device to be installed in, for example, a medical institution to retain pharmaceutical(s) 300 (pharmaceutical product(s)) produced by pharmaceutical manufacturer(s) and delivered by pharmaceutical wholesaler(s), for storage and management of the pharmaceutical(s) 300 under an environment at an optimum refrigerating temperature(s).

The pharmaceutical refrigerator 100 includes an outer case 110, an inner case 120, a machinery room 130, a door 140, a temperature sensor 150, and a door sensor 160.

The outer case 110 has a rectangular parallel piped shape with an opening 111 in its front face for carrying pharmaceutical(s) 300 in and out.

The inner case 120 has a rectangular parallel piped shape with an opening 121 in its front face in communication with the opening 111. The inner case 120 is provided in the outer case 110 with a heat insulating material provided therebetween. The inner case 120 has multiple shelves 122 for keeping pharmaceutical storage boxes 200. Ventilation holes are provided in the horizontal surfaces of the shelves 122 in the form of, for example, a mesh to ensure ventilation.

The machinery room 130 is formed, below the inner case 120, in the outer case 110, and a cooling device (not illustrated) is provided to refrigerate the inner case 120. The cooling device circulates a coolant using, for example, a compressor, condenser, evaporator, and the like, and is coupled to the inner case 120 so that air at a predetermined refrigerating temperature circulates in the inner case 120.

The pharmaceutical refrigerator 100 has the door 140 that opens and closes when a pharmaceutical storage box 200 is to be placed on the shelf 122 in the pharmaceutical refrigerator 100 or when the pharmaceutical(s) 300 is/are carried in or out of the pharmaceutical storage box(es) 200 in the pharmaceutical refrigerator 100. The door 140 has a glass window 141 for checking the inside of the inner case 120 and is slidably attached to the opening 111 of the outer case 110. The inner case 120 can be used as a sealed space to refrigerate the pharmaceutical(s) 300, with the door 140 closed.

The temperature sensor 150 is to sense the temperature inside the pharmaceutical storage box(es) 200 placed on the shelf/shelves 122 of the pharmaceutical refrigerator 100. There may be a single sensor or multiple sensors as the temperature sensor 150. The pharmaceutical refrigerator 100 may be designed to accommodate one pharmaceutical storage box 200 or multiple pharmaceutical storage boxes 200.

For example, when one temperature sensor 150 is used for a pharmaceutical refrigerator 100 designed to accommodate one pharmaceutical storage box 200, the temperature sensor 150 may be integrally provided with the pharmaceutical storage box 200 or mounted on, for example, the inner surface of the inner case 120 closest to the pharmaceutical storage box 200.

Additionally, for example, when a single temperature sensor 150 is used for a pharmaceutical refrigerator 100 that is designed to accommodate multiple pharmaceutical storage boxes 200, the temperature sensor 150 should be mounted at a predetermined position in the inner case 120 at which variations in error between actual temperatures in all the pharmaceutical storage boxes 200 and the temperature sensed by the temperature sensor 150 become minimal.

Furthermore, for example, when using the same number of temperature sensors 150 as the number of pharmaceutical storage boxes 200 in a pharmaceutical refrigerator 100 that is designed to accommodate multiple pharmaceutical storage boxes 200, these temperature sensors 150 may be integrally provided with the pharmaceutical storage boxes 200, respectively, or they may be mounted at predetermined positions in the inner case 120 near the pharmaceutical storage boxes 200, respectively.

The above cases are mere examples. The temperature(s) of the pharmaceutical(s) 300 in the pharmaceutical storage box(es) 200 can be sensed with high accuracy, by appropriately changing the number of temperature sensors 150 and their mounting positions relative to the inner case 120, according to the number of pharmaceutical storage boxes 200 in the pharmaceutical refrigerator 100 and their positions in the pharmaceutical refrigerator 100.

Examples of the temperature sensor 150 to be employed include a sensor with a glycol bottle capable of sensing the temperature of the pharmaceutical 300 without being affected by temperature changes caused by the opening and closing of the door 140 of the pharmaceutical refrigerator 100 or by air circulation in the pharmaceutical refrigerator 100. Examples of the temperature sensor 150 further include a temperature data logger with a built-in temperature sensor 150. The temperature data logger is a device that periodically senses the ambient temperature by a temperature sensor 150 at each predetermined sampling period and accumulates and records the sensed temperatures as data.

The door sensor 160 senses the opening and closing of the door 140 and is attached to an inner side surface of the opening 111. The door sensor 160 is configured using, for example, a microswitch. When the door sensor 160 is a microswitch, it is activated, for example, in response to the door 140 contacting the microswitch with the door 140 being closed, to thereby generate a close signal indicating that the door 140 is closed. On the other hand, when the door 140 is moved away from the microswitch with the door 140 being opened, the microswitch is turned off, for example, to thereby generate an open signal indicating that the door 140 is open.

<<Pharmaceutical Storage Box>>

Figure 4:
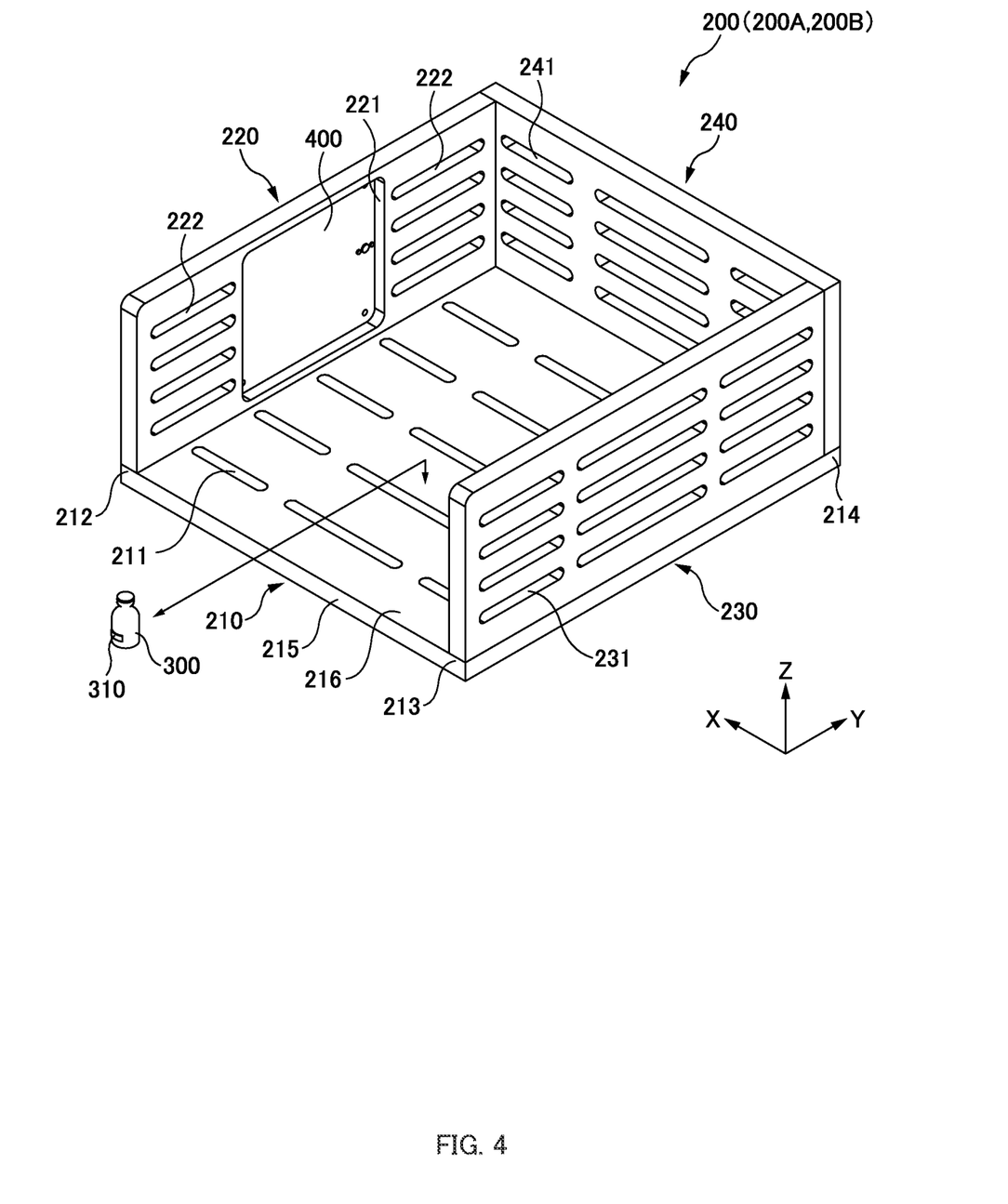
FIG. 4 is a perspective view illustrating an example of a pharmaceutical storage box to be used in a pharmaceutical management system according to an embodiment of the present disclosure.

FIG. 4 is a perspective view illustrating an exemplified pharmaceutical storage box 200 to be used in the pharmaceutical management system 1 according to an embodiment of the present disclosure. In FIG. 4, the X-, Y-, and Z-axes are along the width, depth, and height directions of the pharmaceutical storage box 200, respectively.

Here, in FIG. 1, two pharmaceutical storage boxes 200A and 200B are illustrated. The pharmaceutical storage box 200A is placed in the pharmaceutical refrigerator 100 to manage pharmaceutical(s) 300 under a constant refrigerating temperature. In contrast, the pharmaceutical storage box 200B is placed outside the pharmaceutical refrigerator 100, such as in a hospital ward, and is used to manage pharmaceutical(s) 300 that does/do not need such strict control conditions as those for the pharmaceutical(s) 300 in the pharmaceutical storage box 200A.

Although pharmaceutical storage boxes 200A and 200B are placed at different sites, inside and outside of the pharmaceutical refrigerator 100, respectively, they can have the same configuration. For ease of explanation, the term "pharmaceutical storage box 200," "pharmaceutical storage boxes 200," or "pharmaceutical storage box(es) 200" is used to collectively refer to the pharmaceutical storage boxes 200A and 200B. Pharmaceutical(s) 300A is/are stored in the pharmaceutical storage box 200A, and IC tag(s) 310A is/are attached to the pharmaceutical(s) 300A, respectively. Pharmaceutical(s) 300B is/are stored in the pharmaceutical storage box(es) 200B, and IC tag(s) 310B is/are attached to the pharmaceutical(s) 300B, respectively. The term "pharmaceutical 300," "pharmaceuticals 300," or "pharmaceutical(s) 300" is used to collectively refer to the pharmaceuticals 300A and 300B, and the term "IC tag 310," "IC tags 310," or "IC tag(s) 310" is used to collectively refer to the IC tags 310A and 310B. Furthermore, antennas 400A and 400B are attached to the pharmaceutical storage boxes 200A and 200B, respectively, and the term "antenna 400," "antennas 400," or "antenna(s) 400" is used to collectively refer to the antennas 400A and 400B.

The pharmaceutical storage boxes 200 are to store pharmaceuticals 300 to be managed.

Each pharmaceutical storage box 200 includes a bottom plate 210, a first side plate 220, a second side plate 230, a back plate 240, and an antenna 400.

The bottom plate 210 is of a plate material having a flat plate shape, and pharmaceutical(s) 300 is/are to be placed thereon. The bottom plate 210 is formed by, for example, molding using a mold and a resin material. A surface of the bottom plate 210, depicted on the upper side (+Y side) of the paper plane, is formed to be flat so that pharmaceuticals 300 can be stably placed thereon.

A plurality of ventilation holes 211 is formed in the bottom plate 210, so as to pass through the bottom plate 210 in a thickness direction thereof (along the Z-axis) such that the pharmaceutical(s) 300 placed on the bottom plate 210 can be effectively refrigerated by the refrigerating air circulating in the inner case 120. The ventilation holes 211 each are in the form of, for example, a slit that is an elongated hole and are aligned at regular intervals in the bottom plate 210, such that pharmaceutical 300 will not be inclined even if riding up on a ventilation hole 211 when placed on the bottom plate 210.

The first side plate 220 is a flat-plate-shaped member that rises upwardly (+Z side) from an end surface 212 of the bottom plate 210 on the left side (+X side) of the paper plane along the depth direction (along the Y-axis). The first side plate 220 is, similarly to the bottom plate 210, formed by molding using a mold and a resin material.

Here, an IC tag 310 is attached to each pharmaceutical 300 placed on the bottom plate 210 to identify such pharmaceutical 300. In an embodiment of the present disclosure, the IC tag 310 is, for example, a passive-type RFID tag with a loop coil and IC chip. Each IC chip contains ID information stored therein in advance to represent the corresponding pharmaceutical 300. Each IC chip contains, as ID information stored therein in advance, a "product code" assigned to the corresponding pharmaceutical 300, a "pharmaceutical name," a "manufacturer code" indicating a pharmaceutical manufacturer, a "date of receipt" of the corresponding pharmaceutical 300, an "expiration date" of the corresponding pharmaceutical 300, a "lot number" of the corresponding pharmaceutical 300, and the "image data" of the corresponding pharmaceutical 300, and the like.

Each antenna 400 is a device to transmit radio waves into the space surrounded by the bottom plate 210, the first side plate 220, the second side plate 230, and the back plate 240, to thereby activate the IC chip in the IC tag 310 attached to each pharmaceutical 300, and to receive the ID information indicating the corresponding pharmaceutical 300. The ID information received by the antenna(s) 400 is managed by the controller described below in association with the information indicating the time at which the corresponding pharmaceutical 300 has been carried in/out and the cooling temperature of the pharmaceutical 300. The antennas 400 have a flat plate shape.

The first side plate 220 has a depression 221 in its thickness direction (along the X-axis) to house an antenna 400. The depth of the depression 221 (along the X-axis) is larger than the thickness of the antenna 400. In other words, the antenna 400 is embedded without protruding from the depression 221 when it is received and secured to the depression 221. This is to avoid the antenna 400 from being unable to receive the ID information of the pharmaceutical(s) 300 correctly, due to reduction in reception sensitivity of the antenna 400 caused by the pharmaceutical(s) 300 contacting the antenna 400.

Additionally, a plurality of ventilation holes 222 is formed in the first side plate 220, so as to pass therethrough in the thickness direction thereof such that the pharmaceutical(s) 300 can be effectively refrigerated by the air circulating in the inner case 120. The ventilation holes 222 each are in the form of, for example, a slit that is an elongated hole, and are aligned at regular intervals in the areas on both sides (+Y side and −Y side) of the antenna 400 such that the antenna 400 is sandwiched therebetween.

The second side plate 230 is a flat-plate-shaped member that rises upwardly (+Z side) from another end surface 213 of the bottom plate 210 on the right side (−X side) of the paper plane along the depth direction (along the Y-axis). The second side plate 230 is, similarly to the bottom plate 210, formed by molding using a mold and a resin material.

A plurality of ventilation holes 231 is formed in the second side plate 230, so as to pass therethrough in the thickness direction thereof such that the pharmaceutical(s) 300 can be effectively refrigerated by the air circulating in the inner case 120. The ventilation holes 231 each are in the form of, for example, a slit that is elongated hole, and are aligned at regular intervals.

The back plate 240 is a flat-plate-shaped member that rises upwardly (+Z side) from yet another end surface 214 of the bottom plate 210 on the back side (+Y side) of the paper plane along the width direction (along the X-axis). The back plate 240 is, similarly to the bottom plate 210, formed by molding using a mold and a resin material.

A plurality of ventilation holes 241 is formed in the back plate 240, so as to pass therethrough in the thickness direction thereof (along the Y-axis) such that the pharmaceutical(s) 300 can be effectively refrigerated by the air circulating in the inner case 120. The ventilation holes 241 each are in the form of, for example, a slit that is an elongated hole, and are aligned at regular intervals.

Although not illustrated, the bottom plate 210 has engagement pieces and notches for coupling itself to the first side plate 220, the second side plate 230, and the back plate 240. The first side plate 220 and the second side plate 230 have engagement pieces and notches for coupling themselves to the bottom plate 210 and the back plate 240. The back plate 240 has engagement pieces and notches for coupling itself to the bottom plate 210, the first side plate 220, and the second side plate 230. These four flat plates that are the bottom plate 210, the first side plate 220, the second side plate 230, and the back plate 240 are assembled as illustrated in FIG. 4, thereby completing a pharmaceutical storage box 200 with a storage space defined by the four flat plates for storing pharmaceutical(s) 300.

In each pharmaceutical storage box 200, a delivery entrance 216 for pharmaceutical(s) 300 is formed, without providing an upright flat plate, at an end surface 215 of the bottom plate 210 on the front side (−Y side) of the paper plane opposite to the back plate 240 that is along the width direction. The pharmaceutical storage box 200 should be placed such that the delivery entrance 216 faces the door 140 when it is placed in the pharmaceutical refrigerator 100. This makes it possible for users to open the door 140 of the pharmaceutical refrigerator 100 and carry the pharmaceutical(s) 300 in and out of the pharmaceutical storage box 200. Additionally, since the antenna 400 is attached so as to face the storage space for pharmaceutical(s) 300, it is possible to receive ID information from the IC tag(s) 310 attached to the pharmaceutical(s) 300 without fail.

<<RFID Reader/Writer>>

The RFID reader/writer 500 is a device used to write and read data to and from the IC tag(s) 310 attached to the pharmaceutical(s) 300 stored in the pharmaceutical storage box(es) 200 through the antenna(s) 400. When updating information related to the pharmaceutical 300 stored in the corresponding IC tag 310, for example, the RFID reader/writer 500 transmits ID information to be updated to the corresponding IC tag 310 through the antenna 400. In addition, for example, when managing the entry/exit of the pharmaceutical(s) 300, the RFID reader/writer 500 obtains ID information stored in the IC tag(s) 310 of the pharmaceuticals 300 in the pharmaceutical storage box(es) 200 through the antenna(s) 400. The RFID reader/writer 500 and the antenna(s) 400 are connected via a coaxial cable. The RFID reader/writer 500 and the antenna(s) 400 constitute a reading device.

<<Controller>>

The controller 600 is a device to obtain ID information stored in the IC tags 310 from the pharmaceutical storage box(es) 200 and manage the obtained information in association with the refrigerating temperature(s) for the pharmaceutical(s) 300 and the information about the entry/exit of the pharmaceutical(s) 300, for example.

When the controller 600 obtains ID information stored in the IC tag(s) 310 of the pharmaceutical(s) 300, the following issues may arise due to leakage of radio waves from the antenna(s) 400 to the outside of the pharmaceutical refrigerator 100. For example, when the pharmaceutical 300 that is not to be managed is temporarily placed outside the pharmaceutical refrigerator 100 (e.g., in front of the door 140), the antenna 400 may receive ID information from the IC tag 310 of this pharmaceutical 300. Here, the pharmaceutical 300 may be misjudged as if it has been carried in the pharmaceutical storage box 200, and this may make it impossible to grasp the entry status of the pharmaceutical (s) in the pharmaceutical storage box 200 accurately.

Additionally, failure of the IC tag 310 may make it impossible for the antenna 400 to receive the ID information of the pharmaceutical 300 even though the pharmaceutical 300 is in a pharmaceutical storage box 200. In such a case, the pharmaceutical 300 may be misjudged as if it has been moved out of the pharmaceutical storage box 200, which may make it impossible to grasp the entry status of the pharmaceutical (s) in the pharmaceutical storage box 200 accurately.

Moreover, the antenna 400 may suffer from the so-called chattering, that is, a repeat of receiving and not receiving ID information from the IC tag 310 due to the influence of moisture contained in the pharmaceutical 300 or metal cap for opening and closing a container (e.g., a vial bottle) in which the pharmaceutical 300 is enclosed. In such a case, this pharmaceutical 300 may be misjudged as if it has been carried out of the pharmaceutical storage box 200, which may make it impossible to grasp the entry status of the pharmaceutical(s) in the pharmaceutical storage box 200 accurately.

The controller 600 is configured so as to solve these issues. A specific configuration of the controller 600 will be described below.

The controller 600 includes an input unit 610, a first entry/exit monitoring unit 620, a second entry/exit monitoring unit 630, a timer unit 640, a display unit 650, and a memory unit 660.

As described above, the pharmaceutical storage box 200A is in the pharmaceutical refrigerator 100, and the pharmaceutical storage box 200B is outside the pharmaceutical refrigerator 100. The controller 600 performs control so as to manage the status of the entry/exit of pharmaceuticals 300A and 300B into/from the pharmaceutical storage boxes 200A and 200B, respectively. The difference in the control performed by the controller 600 so as to manage the status of the entry/exit of pharmaceuticals 300A and 300B into/from the pharmaceutical storage boxes 200A and 200B is that an open/close signal from the door sensor 160 is used in the case of the pharmaceutical storage box 200A, and no open/close signal from the door sensor 160 is used in the case of the pharmaceutical storage box 200B because the pharmaceutical storage box 200B is placed outside the pharmaceutical refrigerator 100. In managing the status of the entry/exit of pharmaceutical(s) 300B into/from the pharmaceutical storage box 200B, the controller 600 assumes that there is a virtual door equivalent to the door 140, and obtains a trigger signal to determine the opening/closing of this virtual door, instead of the open/close signal from the door sensor 160. Since the virtual door should be opened when carrying the pharmaceutical(s) 300B in or out of the pharmaceutical storage box 200B, the controller 600 needs to obtain the trigger signal to determine that the virtual door is open. Meanwhile, since the virtual door should be closed when the entry/exit of pharmaceutical(s) 300B into/from the pharmaceutical storage box 200B is completed, the controller 600 needs to obtain the trigger signal to determine that the virtual door is closed.

The trigger signal to determine whether the virtual door is open or closed is input to the input unit 610 through an input operation by an operator. The input unit 610 includes, for example, a display screen that allows input operations of a touch-panel type. The display screen displays an icon indicating that the virtual door is open and an icon indicating that the virtual door is closed. The trigger signal may be input in response to the operator selectively touching these icons. The display screen also displays other icons for input operations needed for the controller 600 to manage the status of the entry/exit of the pharmaceutical(s) 300 into/from the pharmaceutical storage box(es) 200.

The temperature data indicating the temperature sensed by the temperature sensor 150 in the pharmaceutical refrigerator 100 is transmitted from a communication box 170 provided in the pharmaceutical refrigerator 100 and then sent to the controller 600 through a HUB 800. The open/close signal from the door sensor 160 is also transmitted from the communication box 170 to the controller 600 through the HUB 800. The ID information of each pharmaceutical 300 read by the RFID reader/writer 500 is transmitted to the controller 600 through the HUB 800. The HUB is connected to each of the communication box 170, the RFID reader/writer 500, the controller 600 by a local area network (LAN) communication. As such, the controller 600 receives data of temperature in the pharmaceutical refrigerator 100, the open/close signal for the door 140, ID information of the pharmaceuticals 300, and the trigger signal to determine the opening and closing of the virtual door.

In response to the controller 600 obtaining the close signal indicating that the door 140 has been closed from an open state, or in response to the controller 600 obtaining the trigger signal to determine that the virtual door has been closed from an open state, the timer unit 640 start measuring a first period (e.g. 6 seconds) so that the first entry/exit monitoring unit 620 can monitor the state of the entry/exit of the pharmaceutical(s) 300 into/from the pharmaceutical storage box(es) 200. Specifically, in measuring the first period, the timer unit 640 operates to periodically measure a time period (e.g., 30 seconds) longer than the first period. Here, the first period is the first 6-second segment of the measurement time period of the first time cycle. The second period used for the second entry/exit monitoring unit 630 to monitor the state of the entry/exit of the pharmaceutical(s) 300 into/from the pharmaceutical storage box(es) 200 is a set of the remaining segment (24 seconds) of the measurement time period of the first time cycle and the measurement time periods (30 seconds each) of the second and subsequent time cycles. As such, the second period is set to be longer than the first period.

The timer unit 640 starts measuring the time in response to the input unit 610 starting to obtain the close signal from the door sensor 160 from a state of obtaining the open signal from the door sensor 160, when an operator carries the pharmaceutical(s) 300A in or out of the pharmaceutical storage box(es) 200A. At this time, the first entry/exit monitoring unit 620 obtains ID information from the IC tag(s) 310A of the pharmaceutical(s) 300A in the pharmaceutical storage box(es) 200A during the first period, which is the first partial segment of the measurement time period of the first time cycle in the time periods measured periodically by the timer unit 640. As will be described later, the state of entry of the pharmaceutical(s) 300A in the pharmaceutical storage box(es) 200A is periodically determined based on the result of monitoring by the second entry/exit monitoring unit 630. Accordingly, the first entry/exit monitoring unit 620 monitors whether any pharmaceutical(s) 300A has/have newly been carried in or out by obtaining all the ID information from the IC tags 310A of all the pharmaceuticals 300A stored in the pharmaceutical storage box(es) 200A and comparing the obtained information with information on the state of entry of the pharmaceutical(s) 300A in the pharmaceutical storage box(es) 200A having been already determined at this point.

Similarly, the timer unit 640 starts measuring the time in response to the input unit 610 starting to obtain the trigger signal to determine that the virtual door is closed from a state of obtaining the trigger signal to determine that the virtual door is open, when an operator carries pharmaceutical(s) 300B in or out of the pharmaceutical storage box(es) 200B. At this time, the first entry/exit monitoring unit 620 obtains ID information from the IC tag(s) 310B of the pharmaceutical(s) 300B in the pharmaceutical storage box(es) 200B during the first period, which is the first partial segment of the measurement time period of the first time cycle in the time periods measured periodically by the timer unit 640. Here, the state of entry of the pharmaceutical(s) 300B in the pharmaceutical storage box(es) 200B is periodically determined based on the result of monitoring by the second entry/exit monitoring unit 630. Accordingly, the first entry/exit monitoring unit 620 monitors whether any pharmaceutical(s) 300B has/have newly been carried in or out by obtaining all the ID information from the IC tags 310B of all the pharmaceuticals 300B stored in the pharmaceutical storage box(es) 200B and comparing the obtained information with information on the state of entry of the pharmaceutical(s) 300B in the pharmaceutical storage box(es) 200B having been already determined at this point.

After a lapse of the first period, the state of entry of the pharmaceutical(s) 300 assumed to remain in the pharmaceutical storage box(es) 200, taking into account the pharmaceutical(s) 300 determined to have been newly carried in or out as the result of monitoring by the first entry/exit monitoring unit 620, is displayed on the display unit 650, such as a display screen. Accordingly, the operator can check, through the display unit 650, the state of entry after the actual entry/exit of the pharmaceutical(s) 300 into/from the pharmaceutical storage box(es) 200. Here, the first period is, for example, 6 seconds as explained earlier. This 6-second segment is set as a time period for the operator to be likely to feel relatively less stress from when the operator closes the door 140 to when the operator confirms the state of entry of the pharmaceutical(s) 300A in the pharmaceutical storage box(es) 200A through the display unit 650, or from the time the operator operates and inputs the trigger signal to determine that the virtual door is closed to when the operator confirms the state of entry of the pharmaceutical(s) 300B in the pharmaceutical storage box(es) 200B through the display unit 650.

The above first period is the minimum period. The first entry/exit monitoring unit 620 may obtain ID information from the IC tag(s) 310 of the pharmaceutical(s) 300 stored in the pharmaceutical storage box(es) 200 until the first period has passed, in other words, over a time period longer than the first period.

The second entry/exit monitoring unit 630 monitors the entry/exit of the pharmaceutical(s) 300 into/from the pharmaceutical storage box(es) 200 by obtaining the ID information of IC tag(s) 310 for a second period measured by the timer unit 640 after the first entry/exit monitoring unit 620 finishes monitoring.

The controller 600 needs to avoid incorrect determination on entry/exit in both of the following cases: a case in which the second entry/exit monitoring unit 630 obtains new ID information when comparing the result of monitoring with the state of entry of the pharmaceutical(s) 300 in the pharmaceutical storage box(es) 200, which is the result of monitoring by the first entry/exit monitoring unit 620; and a case in which ID information becomes unable to be obtained even though it is the ID information of the pharmaceutical(s) 300 determined to be carried in by the first entry/exit monitoring unit 620.

The following are examples of possible cases in which the second entry/exit monitoring unit 630 obtains new ID information. For example, in the case of the pharmaceutical storage box 200A placed inside the pharmaceutical refrigerator 100, the ID information of the pharmaceutical(s) 300A that is/are not to be managed and thus has/have already been carried out and temporarily placed near the pharmaceutical refrigerator 100 may be obtained mistakenly due to the leakage of radio waves from the antenna 400A to the outside of the pharmaceutical refrigerator 100. In this case, it is needed not to judge the pharmaceutical(s) 300A that is/are not to be managed as having been carried in, because the pharmaceutical(s) 300A is/are placed outside the door 140.

Additionally, for example, in the case of the pharmaceutical storage box 200B placed outside the pharmaceutical refrigerator 100, even after the first entry/exit monitoring unit 620 finishes monitoring, an operator may carry the pharmaceutical(s) 300B that the operator wants to manage into the pharmaceutical storage box 200B, and ID information thereof may be obtained as new one because there is no physical door. Even though the controller 600 has already obtained the trigger signal to determine that the virtual door has been closed, this pharmaceutical(s) 300 B must be judged as having been carried in.

Thus, the second entry/exit monitoring unit 630 can be set to a mode of determining whether new ID information has been continuously obtained for the second period, in order to determine the entry/exit of a pharmaceutical(s) 300B after obtaining new ID information. The mode can be set by operating the input unit 610 when the state of entry of the pharmaceutical(s) 300B into the pharmaceutical storage box(es) 200B is determined.

When the above-mentioned mode is not set, the controller 600 deletes new ID information without adding it to the state of entry of the pharmaceutical(s) 300, which is the result of monitoring by the first entry/exit monitoring unit 620, even if the second entry/exit monitoring unit 630 obtains the new ID information. The controller 600 then determines the state of entry of the pharmaceutical(s) 300A into the pharmaceutical storage box(es) 200A.

In contrast, when the above-mentioned mode is set, the second entry/exit monitoring unit 630 determines whether new ID information can be continuously obtained for the second period. When the second entry/exit monitoring unit 630 continuously obtains new ID information for the second period, the controller 600 adds the new ID information to the state of entry of the pharmaceutical(s) 300B, which is the result of monitoring by the first entry/exit monitoring unit 620. The controller 600 then determines the state of entry of the pharmaceutical(s) 300B into the pharmaceutical storage box 200B.

Examples of possible cases in which the second entry/exit monitoring unit 630 becomes unable to obtain the already-existing ID information include the case in which the IC tag 310 is faulty or the antenna 400 suffers from chattering, that is, a repeat of receiving and not receiving ID information from the IC tag 310 due to the influence of moisture contained in the pharmaceutical 300 or metal cap for opening and closing a container in which the pharmaceutical 300 is enclosed. In these cases, when the second entry/exit monitoring unit 630 cannot continuously obtain the already-existing ID information for the second period, the controller 600 determines the state of entry of the pharmaceutical(s) 300 into the pharmaceutical storage box(es) 200, assuming that whether the IC tag 310 storing the ID information that becomes unable to be obtained is faulty or the pharmaceutical 300 attached with this IC 310 has been carried out, with respect to the state of entry of the pharmaceutical(s) 300 that is the result of monitoring by the first entry/exit monitoring unit 620. When the already-existing ID information cannot be continuously obtained for the second period in the pharmaceutical storage box(es) 200A, the controller 600 determines that the IC tag(s) 310A storing this ID information has failed. Meanwhile, when the already-existing ID information cannot be continuously obtained for the second period in the pharmaceutical storage box(es) 200B, the controller 600 determines that the IC tag 310B storing this ID information is faulty, or that the pharmaceutical 300B attached with this IC tag 310B has been carried out.

The result of monitoring by the second entry/exit monitoring unit 630 is displayed on the display unit 650 so that an operator can visually check the result in the same manner as the result of monitoring by the first entry/exit monitoring unit 620.

Note that the second period herein is a time period for the second entry/exit monitoring unit 630 to obtain ID information from the IC tag(s) 310 of the pharmaceutical(s) 300 in the pharmaceutical storage box(es) 200. This time period should be set to an appropriate time period within the second period.

The controller 600 comprises a microcomputer. The functions and operations of the input unit 610, the first entry/exit monitoring unit 620, the second entry/exit monitoring unit 630, the timer unit 640, and the display unit 650, which configure the controller 600 are achieved by software processing of a program stored in the memory unit 660.

The storage device 700 is connected to the controller 600 via a LAN through a HUB 800. The controller 600 obtains ID information stored in each IC tag 310 from the pharmaceutical storage box(es) 200, and associates the obtained information with the refrigerating temperature and the information on the entry/exit of the corresponding pharmaceutical 300. The associated information is stored in the storage device 700 through the HUB 800.

A router 900 (e.g., LTE router) is connected to the HUB 800 through a LAN and is linked to other computers and the like in the cloud via the Internet or other networks.

===Operation of Controller===

Figure 5:
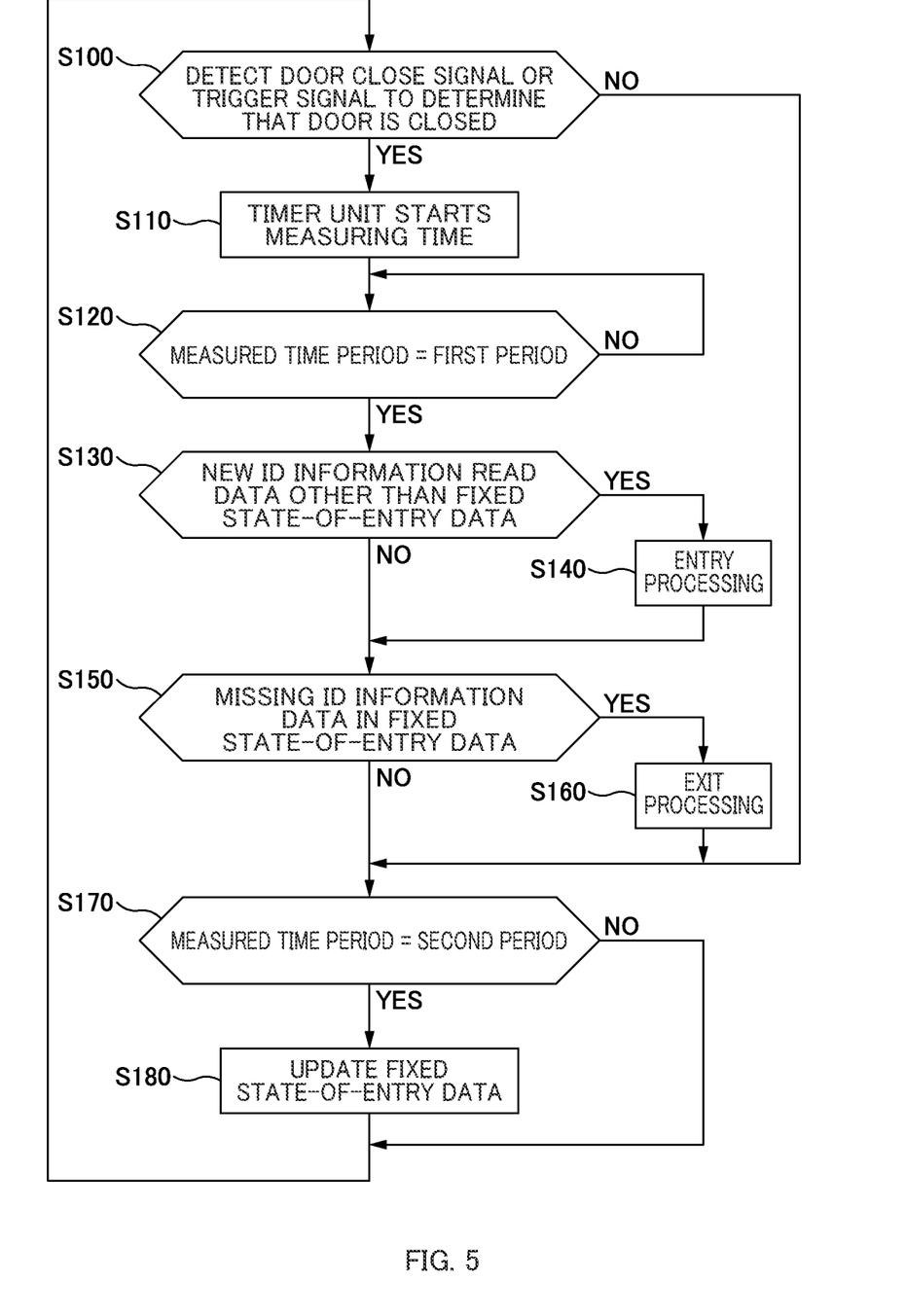
FIG. 5 is a flowchart illustrating an operation of determining a state of entry of pharmaceutical(s) into a pharmaceutical storage box based on the results of monitoring by first and second entry/exit monitoring units in a pharmaceutical management system according to an embodiment of the present disclosure.

FIG. 5 is a flowchart illustrating a basic process flow carried out by the controller 600 to determine the state of entry of the pharmaceutical(s) 300 in the pharmaceutical storage box(es) 200 based on the results of monitoring by the first entry/exit monitoring unit 620 and the second entry/exit monitoring unit 630.

First, to carry the pharmaceutical(s) 300A in and out of the pharmaceutical storage box(es) 200A, an operator opens the door of the pharmaceutical refrigerator 100 and carries the pharmaceutical(s) 300A in or out of the pharmaceutical storage box(es) 200A. At this time, the door sensor 160 outputs the open signal indicating that the door 140 is open. The controller 600 obtains this open signal through the communication box 170 and the HUB 800. After carrying the pharmaceutical(s) 300A in or out of the pharmaceutical storage box(es) 200A, the operator closes the door 140. At this time, the door sensor 160 outputs the close signal indicating that the door 140 is closed. The controller 600 obtains this close signal through the communication box 170 and the HUB 800.

Meanwhile, to carry the pharmaceutical(s) 300B in or out of the pharmaceutical storage box(es) 200B, there is no door such as the door 140 to be opened and closed when carrying the pharmaceutical(s) 300A in or out of the pharmaceutical storage box(es) 200A. Accordingly, to carry the pharmaceutical(s) 300B in or out of the pharmaceutical storage box(es) 200B, the operator operates and inputs, through the input unit 610, the trigger signal to determine that the virtual door is open. The controller 600 obtains this trigger signal. Upon completion of carrying of the pharmaceutical(s) 300B in or out of the pharmaceutical storage box 200B, the operator operates and inputs, through the input unit 610, the trigger signal to determine that the virtual door is closed. The controller 600 obtains this trigger signal.

In other words, the controller 600 detects whether the close signal from the door sensor 160 has been obtained when the pharmaceutical(s) 300A is/are carried in or out of the pharmaceutical storage box 200A. Meanwhile, the controller 600 detects whether the trigger signal to determine that the virtual door is closed, which is input through the input unit 610, has been obtained when the pharmaceutical(s) 300B is/are carried in or out of the pharmaceutical storage box 200B (step S100).

Here, the processes from step S110 are common processes in determining the state of entry of pharmaceuticals 300A and 300B in the pharmaceutical storage boxes 200A and 200B, and these boxes are thus collectively referred to as "pharmaceutical storage box(es) 200" without distinction.

When the controller 600 obtains the above-mentioned close signal or trigger signal (step S100: YES), the controller 600 instructs the timer unit 640 to start measuring the time in response to the close signal or the trigger signal. Thus, the timer unit 640 starts measuring the time to measure the second period periodically. At the same time when the timer unit 640 starts measuring the time, the first entry/exit monitoring unit 620 obtains all the ID information from the IC tags 310 attached to the pharmaceuticals 300 stored in the pharmaceutical storage box(es) 200 during the first period, which is the first partial segment in the second period in the first cycle. Then, it compares obtained information with fixed state-of-entry data of the pharmaceuticals 300 already determined based on the result of monitoring by the second entry/exit monitoring unit 630 (collective data of ID information indicating the pharmaceuticals 300 determined as being stored in the pharmaceutical storage box(es) 200) (step S110).

When the time period measured by the timer unit 640 has passed the first period (step S120: YES), the controller 600 refers to the result of monitoring by the first entry/exit monitoring unit 620, to determine whether the first entry/exit monitoring unit 620 has obtained any new ID information other than the fixed state-of-entry data of the pharmaceuticals 300 (step S130).

When the first entry/exit monitoring unit 620 has obtained new ID information other than the fixed state-of-entry data of the pharmaceuticals 300 (step S130: YES), the controller 600 processes, assuming that the pharmaceutical(s) 300 indicated by the new ID information has/have been carried into the pharmaceutical storage box(es) 200 (S140).

Meanwhile, when the first entry/exit monitoring unit 620 has not obtained any new ID information other than the fixed state-of-entry data of the pharmaceuticals 300 (step S130: NO), the controller 600 refers to the result of monitoring by the first entry/exit monitoring unit 620, to determine whether the first entry/exit monitoring unit 620 becomes unable to obtain at least part of ID information any more among all the ID information contained in the fixed state-of-entry data of the pharmaceuticals 300 (step S150).

When the first entry/exit monitoring unit 620 becomes unable to obtain at least part of ID information (step S150: YES), the controller 600 processes, assuming that the pharmaceuticals 300 indicated by such at least part of ID information has been carried out from the pharmaceutical storage box(es) 200A (S160).

Meanwhile, when the first entry/exit monitoring unit 620 has obtained all the ID information included in the fixed state-of-entry data (step S150: NO), the process proceeds to step S17, which will be described later.

Here, upon completion of the judgment process in step S150, the state of entry of the pharmaceutical(s) 300 in the pharmaceutical storage box(es) 200, which is the result of monitoring by the first entry/exit monitoring unit 620, is displayed on the display unit 650.

As such, after determining the state of entry of the pharmaceutical(s) 300 in the pharmaceutical storage box(es) 200 based on the result of monitoring by the first warehouse monitoring unit 620, the second entry/exit monitoring unit 630 obtains all the ID information from the IC tags 310 attached to the pharmaceuticals 300 stored in the pharmaceutical storage box 200 while determining whether a time period measured by the timer unit 640 has passed the second period, and compares the obtained information with the fixed state-of-entry data of the pharmaceuticals 300 that has been already determined (step S170).

The process returns to step S100 when the measured time period has not passed the second period (step S170: NO). Here, the close signal indicating that the door 140 is closed and the trigger signal to determine that the virtual door is closed are not detected again, and thus, the process of step S170 is performed again through NO of step S100. When the measured time has passed the second period (step S170: YES), all the ID information of the pharmaceuticals that are considered to be in the pharmaceutical storage box(es) 200 obtained at the time of processing in step S170 are compiled as the fixed state-of-entry data, and the process returns to step S100 (step S180). In other words, the fixed state-of-entry data are updated by the loop processes of steps S100 to S180. This fixed state-of-entry data are stored in the storage device 700 and can be displayed on the display unit 650 upon an operator's request.

Figure 6:
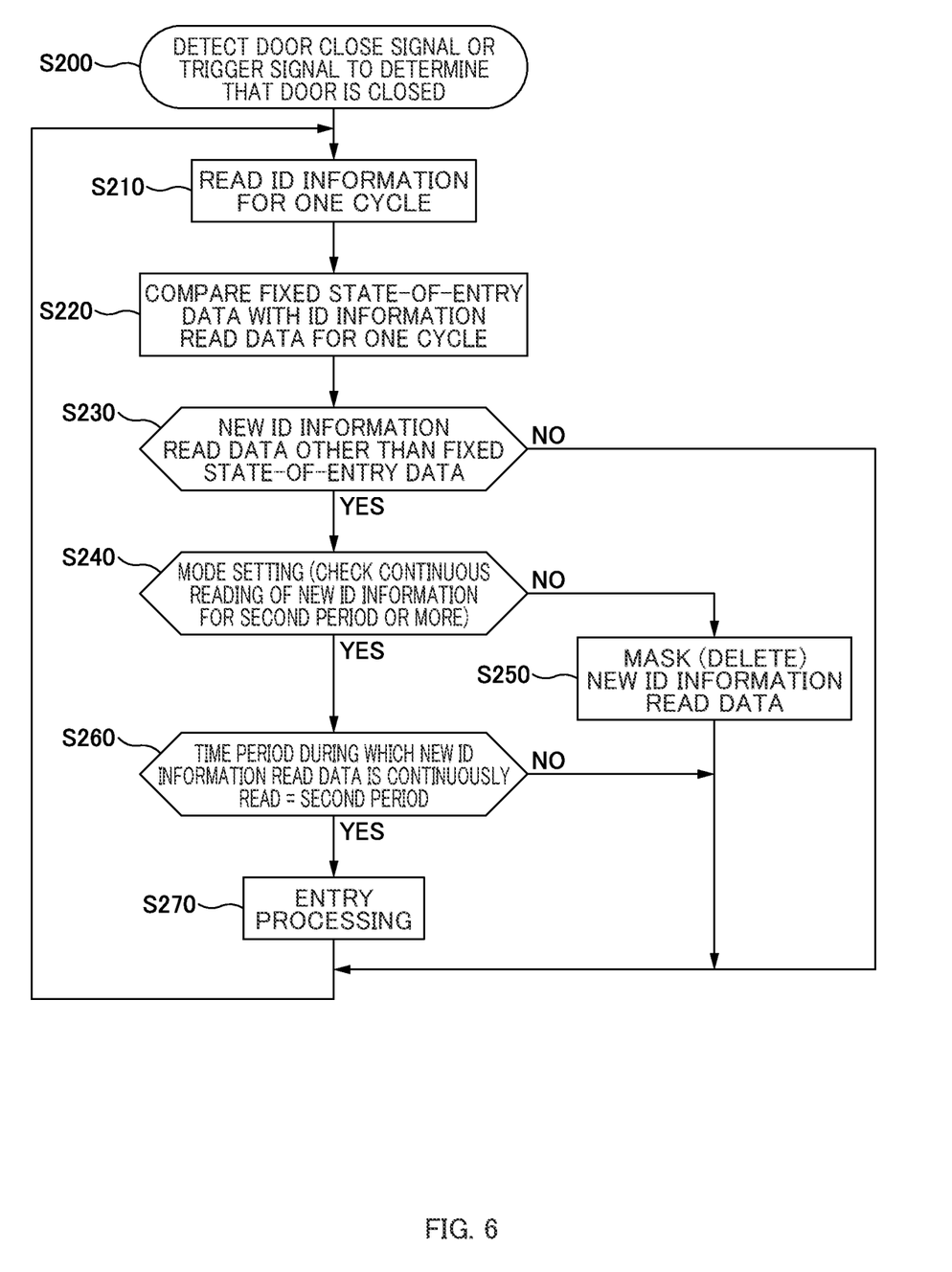
FIG. 6 is a flowchart illustrating an operation of determining a state of entry of pharmaceutical(s) into a pharmaceutical storage box based on the result of monitoring by a second entry/exit monitoring unit in a pharmaceutical management system according to an embodiment of the present disclosure.

FIG. 6 is a flowchart illustrating a process flow carried out by the controller 600 to determine a state of entry of the pharmaceutical(s) 300 in the pharmaceutical storage box(es) 200, based on the result of monitoring by the second entry/exit monitoring unit 630.

First, in performing the process illustrated in FIG. 6, it is assumed that the controller 600 has obtained either the close signal from the door sensor 160 or the trigger signal to determine that the virtual door is closed, as indicated in step S100 in FIG. 5, and that the entry/exit processing for the pharmaceutical(s) 300 with respect to the pharmaceutical storage box(es) 200 by the first entry/exit monitoring unit 620 has been completed. This process is step S200.

In the second entry/exit monitoring unit 630, all the ID information is obtained from the IC tags 310 attached to the pharmaceuticals 300 stored in the pharmaceutical storage box(es) 200 (step S210).

Then, in the second entry/exit monitoring unit 630, the ID information obtained in step S210 is compared with the fixed state-of-entry data of the pharmaceuticals 300 that has been subjected to the entry/exit processing based on the result of monitoring by the first entry/exit monitoring unit 620 (step S220).

The controller 600 determines whether any new ID information has been obtained in addition to the fixed state-of-entry data, as the result of monitoring by the second entry/exit monitoring unit (step S230).

The controller 600 performs the decision in the following step S240 separately for each case of the pharmaceutical storage boxes 200A and 200B when new ID information has been obtained in addition to the fixed state-of-entry data (step S230: YES). For example, when the close signal from the door sensor 160 has been obtained in step S200, the controller 600 does not need to set the second entry/exit monitoring unit 630 to a mode to determine whether new ID information has been continuously obtained for the second period to determine the entry/exit of the pharmaceutical(s) 300A after obtaining new ID information (step S240: NO), because the door 140 must be opened and closed when carrying the pharmaceutical(s) 300A in or out of the pharmaceutical storage box(es) 200A. Thus, in this case, the newly obtained ID information is considered to be obtained from the IC tag(s) or the like attached to the pharmaceutical(s) 300A that is/are not to be managed and thus placed outside the pharmaceutical refrigerator 100, due to the leakage of radio waves from the antenna(s) 400A provided to the pharmaceutical storage box(es) 200A. Accordingly, the controller 600 deletes this new ID information without treating the pharmaceutical(s) 300A indicated by this ID information as having been carried in (step S250). The process then returns to step S210.

Meanwhile, when the trigger signal to determine that the virtual door is closed has been obtained in step S200, the controller 600 sets the second entry/exit monitoring unit 630 to a mode to determine whether new ID information has been continuously obtained for the second period to determine the entry/exit of the pharmaceutical(s) 300B after obtaining new ID information (step S240: YES). When the second entry/exit monitoring unit 630 has continuously obtained new ID information for the second period (step S260: YES). The controller 600 processes, assuming that the pharmaceutical(s) 300B indicated by the new ID information has/have been carried into the pharmaceutical storage box(es) 200B (step S270). The process returns to step S210.

Moreover, when the second entry/exit monitoring unit 630 has not continuously obtained any new ID information for the second period (step S260: NO), the ID information can be considered to be obtained from the IC tag(s) or the like attached to the pharmaceutical(s) 300B that is/are not to be managed and thus placed outside the pharmaceutical storage box(es) 200B, due to the leakage of radio waves from the antenna(s) 400B provided to the pharmaceutical storage box(es) 200B to the outside thereof, for example. Accordingly, the controller 600 deletes this new ID information without treating the pharmaceutical(s) 300B indicated by this ID information as having been carried in. The process returns to step S210.

In this way, the entries of the pharmaceuticals 300A and 300B can be correctly determined in the pharmaceutical storage boxes 200A and 200B, respectively, even if the second entry/exit monitoring unit 630 obtains new ID information.

Figure 7:
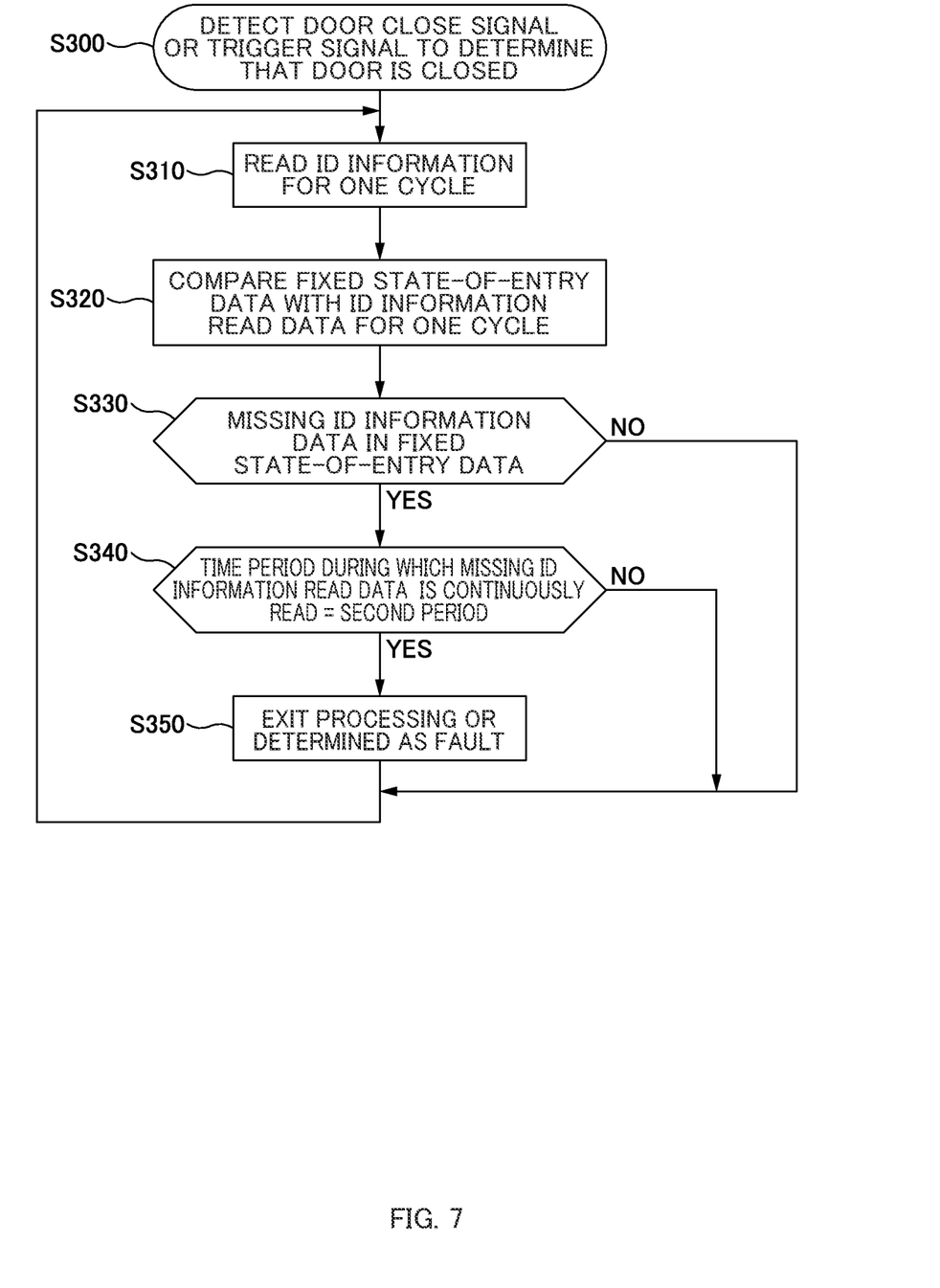
FIG. 7 is a flowchart illustrating another operation of determining a state of entry of pharmaceutical(s) into a pharmaceutical storage box based on monitoring by a second entry/exit monitoring unit in a pharmaceutical management system according to an embodiment of the present disclosure.

FIG. 7 is another flowchart illustrating a process flow carried out by the controller 600 to determine a state of entry of the pharmaceutical(s) 300 in the pharmaceutical storage box(es) 200, based on the result of monitoring by the second entry/exit monitoring unit 630.

First, in performing the process illustrated in FIG. 7, it is assumed that the controller 600 obtained either the close signal from the door sensor 160 or the trigger signal to determine that the virtual door is closed, as indicated in step S100 in FIG. 5, and that the entry/exit processing for the pharmaceutical(s) 300 with respect to the pharmaceutical storage box(es) 200 by the first entry/exit monitoring unit 620 has been completed. This process is step S300.

In the second entry/exit monitoring unit 630, all the ID information is obtained from the IC tags 310 attached to the pharmaceuticals 300 stored in the pharmaceutical storage box(es) 200 (step S310).

Then, in the second entry/exit monitoring unit 630, the ID information obtained in step S310 is compared with the fixed state-of-entry data of the pharmaceuticals 300 that has been subjected to the entry/exit processing based on the result of monitoring by the first entry/exit monitoring unit 620 (step S320).

The controller 600 determines, as the result of monitoring by the second entry/exit monitoring unit, whether any ID information is missing in the fixed state-of-entry data, in other words, whether at least part of ID information in the fixed state-of-entry data becomes unable to be obtained (step S330).

When at least part of ID information in the fixed state-of-entry data becomes unable to be obtained (step S330: YES), the controller 600 determines whether at least part of ID information in the fixed state-of-entry data cannot be continuously obtained for the second period (step S340).

When at least part of ID information in the fixed state-of-entry data cannot be continuously obtained for the second period (step S340 yes), it is determined that the corresponding IC tag(s) 310A is/are faulty in the pharmaceutical storage box(es) 200A. Meanwhile, in the pharmaceutical storage box(es) 200B, it is determined that the corresponding pharmaceutical(s) 300B has/have been carried out or the corresponding IC tag(s) 310B is/are faulty (step S350). Then, the process returns to step S310.

When there is no missing ID information in the fixed state-of-entry data (step S330: NO), the process returns to step S310.

When missing ID information cannot be continuously obtained for the second period (step S340: NO), it is assumed, for example, that chattering, in which an antenna 400 repeats receiving and not receiving ID information due to moisture therein or a metal cap, occurs with respect to the pharmaceutical(s) 300 attached with the IC tag(s) 310 storing the missing ID information. This is not determined as the fault of the ID tag 310. The process then returns to step S310.

As such, it is possible to determine the entries of the pharmaceuticals 300A and 300B into the pharmaceutical storage boxes 200A and 200B, respectively, even if there is missing ID information in the fixed state-of-entry data.

Note that an embodiment of the present disclosure described above is simply to facilitate understanding of the present disclosure and is not in any way to be construed as limiting the present disclosure. The present disclosure may variously be changed or altered without departing from its essential features and encompass equivalents thereof. In an embodiment of the present disclosure, the first and second periods are predetermined time periods, respectively; however, the present disclosure is not limited thereto. For example, assuming that the time period during which the antenna(s) 400 receive(s) the ID information from the IC tags 310 of all the pharmaceuticals 300 stored in the pharmaceutical storage box(es) 200 is one cycle, the first and second periods may be determined by the number of cycles during which the antenna(s) 400 receive(s) the ID information from the IC tags 310.

Accordingly, the present disclosure is directed to provision of a pharmaceutical management system capable of smoothly distributing pharmaceuticals among medical institutions, pharmaceutical wholesalers, and pharmaceutical manufacturers.

According to the present disclosure, it is possible to smoothly distribute pharmaceuticals among medical institutions, pharmaceutical wholesalers, and pharmaceutical manufacturers.

What is claimed is:

1. A pharmaceutical management system comprising:
at least one pharmaceutical storage box to store at least one pharmaceutical having corresponding at least one IC tag attached thereto;
a reading device to read information stored in the IC tag, the information representing the pharmaceutical;
a controller to obtain the information of the IC tag from the reading device, to manage the pharmaceutical; and
a pharmaceutical refrigerator to store the pharmaceutical storage box to refrigerate the pharmaceutical,
the controller comprising:
a first entry/exit monitoring unit to monitor entry/exit of the pharmaceutical into/from the pharmaceutical storage box by obtaining the information of the IC tag, during a first period, in response to open/close information indicating that a door of the pharmaceutical refrigerator has been closed from an open state; and
a second entry/exit monitoring unit to monitor entry/exit of the pharmaceutical into/from the pharmaceutical storage box by obtaining the information of the IC tag, during a second period, after monitoring by the first entry/exit monitoring unit, and wherein
a state of entry of the pharmaceutical into the pharmaceutical storage box is determined based on a result of monitoring by the second entry/exit monitoring unit,
wherein when at least part of the information of the IC tag that has been obtained by the first entry/exit monitoring unit cannot be obtained continuously for a predetermined time period within the second period, in the monitoring by the second entry/exit monitoring unit, the controller determines a state of entry of the pharmaceutical into the pharmaceutical storage box, assuming that the IC tag corresponding to the at least part thereof is faulty or the pharmaceutical corresponding to the at least part thereof has been carried out.

2. The pharmaceutical management system according to claim 1, wherein the second period is longer than the first period.

3. The pharmaceutical management system according to claim 1, wherein
the at least one IC tag comprises at least one new IC tag, and
when the information of the new IC tag that has not been obtained by the first entry/exit monitoring unit has been continuously obtained for the second period, in the monitoring by the second entry/exit monitoring unit, the controller determines a state of entry of the pharmaceutical into the pharmaceutical storage box, including the information of the new IC tag.

4. The pharmaceutical management system according to claim 1, wherein the predetermined time period can be set according to the pharmaceutical stored in the pharmaceutical storage box.

5. The pharmaceutical management system according to claim 1, further comprising:
a display unit to display information on entry/exit of the pharmaceutical into/from the pharmaceutical storage box, the information on the entry/exit being a result of the monitoring by the first entry/exit monitoring unit.

* * * * *